United States Patent
Miyauchi et al.

(10) Patent No.: US 9,341,852 B2
(45) Date of Patent: May 17, 2016

(54) CELL SUBSTRATE INSPECTION SYSTEM AND METHOD

(75) Inventors: Takashi Miyauchi, Kawasaki (JP); Kentaro Miyazaki, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 923 days.

(21) Appl. No.: 13/214,383

(22) Filed: Aug. 22, 2011

(65) Prior Publication Data
US 2012/0069156 A1 Mar. 22, 2012

(30) Foreign Application Priority Data
Sep. 17, 2010 (JP) .................................. 2010-209366

(51) Int. Cl.
H04N 13/04 (2006.01)
G02B 27/22 (2006.01)
G01N 21/95 (2006.01)

(52) U.S. Cl.
CPC .... *G02B 27/2214* (2013.01); *G01N 2021/9513* (2013.01)

(58) Field of Classification Search
CPC .................. G01N 2021/9513; G02B 27/2214
USPC .............................................. 351/51; 348/51
See application file for complete search history.

(56) References Cited

U.S. PATENT DOCUMENTS

| | | | | |
|---|---|---|---|---|
| 6,091,479 A | * | 7/2000 | Frosig et al. | 355/22 |
| 2006/0088206 A1 | * | 4/2006 | Era | 382/154 |
| 2006/0245063 A1 | * | 11/2006 | Ra et al. | 359/619 |
| 2010/0026993 A1 | * | 2/2010 | Kim et al. | 356/124 |
| 2011/0013286 A1 | * | 1/2011 | Chen et al. | 359/619 |

FOREIGN PATENT DOCUMENTS

| | | |
|---|---|---|
| CN | 1925628 A | 3/2007 |
| JP | 8-29361 A | 2/1996 |
| JP | 2009-258582 | 11/2009 |

OTHER PUBLICATIONS

Office Action issued on Sep. 18, 2013 in the counterpart Chinese Application No. 201110222935.0 (with English Translation).

* cited by examiner

*Primary Examiner* — William C Vaughn, Jr.
*Assistant Examiner* — Naod Belai
(74) *Attorney, Agent, or Firm* — Oblon, McClelland, Maier & Neustadt, L.L.P (57) ABSTRACT

According to one embodiment, the system for inspecting a cell substrate is provided. The inspection system includes: a signal generator transmitting to a cell substrate a display signal causing the cell substrate to display a test image; an imaging apparatus capturing the test image displayed on the cell substrate; a parallax image generator arranging the set of parallax image information of the captured test image for each parallax image to generate a parallax image prediction of parallax image which is obtained when the cell substrate is bonded to the lenticular lens; and an interface apparatus displaying the parallax image predictions.

5 Claims, 9 Drawing Sheets

CELL SUBSTRATE INSPECTION SYSTEM AND METHOD

CROSS REFERENCE TO RELATED APPLICATIONS AND INCORPORATION BY REFERENCE

This application is based upon and claims the benefit of priority from prior Japanese Patent Application P2010-209366 filed on Sep. 17, 2010; the entire contents of which are incorporated by reference herein.

FIELD

Embodiments described herein relate generally to the inspection system and the method of the cell substrate used for a three-dimensional image display apparatus.

BACKGROUND

In recent years, three-dimensional image display apparatuses not requiring special glasses are being developed. For example, some integral-imaging 3D image display apparatuses have been developed, in which images taken in plural directions are shown according to the viewing angles to provide a stereoscopic image. The integral-imaging system has a plurality of parallax images and therefore provides motion parallax, in which the image seen by a viewer changes as the viewing point of the viewer moves.

Each integral-imaging 3D image display apparatus is manufactured by bonding a lenticular lens to a planer display substrate such as a liquid crystal panel (hereinafter, referred to as a cell substrate). The influence of defects caused in the cell substrate on each parallax image of the stereoscopic image can be checked by a lighting test which displays an image after the lenticular lens is bonded to the cell substrate.

However, according to such a method of observing each parallax image with the cell substrate being bonded to the lenticular lens, it is not known how each parallax image looks when the cell substrate is defective until the cell substrate is bonded to the lenticular lens. If the cell substrate is defective, the lenticular lens needs to be separated from the cell substrate. In many integral imaging 3D image display apparatuses, the cell substrate and lenticular lens are bonded to each other with an adhesive. Accordingly, it is difficult or impossible to separate the lenticular lens from the cell substrate. If the lenticular lens cannot be separated, the cell substrate and lenticular lens are both disposed of.

Even if the lenticular lens can be separated from the cell substrate, it requires time and good skills to separate the lenticular lens, which is made of a glass component in many cases, from the cell substrate without scratching the same. Accordingly, the method of inspecting a cell substrate for defects after bonding the lenticular lens to the cell substrate requires high manufacturing cost and long manufacturing time.

DETAILED DESCRIPTION

In general, according to one embodiment, a system for inspecting a cell substrate, which is bonded to a lenticular lens for use in an integral-imaging three-dimensional image display apparatus and includes a display region composed of an array of a plurality of sub-regions, each sub-region displaying a set of parallax image information obtained by dividing each of a plurality of parallax images, is provided. The above inspection system includes: a signal generator transmitting to a cell substrate as an inspection object, a display signal causing the cell substrate to display a test image; an imaging apparatus capturing the test image displayed on the cell substrate receiving the display signal; a parallax image generator arranging the set of parallax image information of the captured test image for each parallax image in order to generate a parallax image prediction of parallax image which is obtained when the cell substrate is bonded to the lenticular lens; and an interface apparatus displaying the parallax image predictions.

Hereinafter, a description is given of first to third embodiments with reference to the drawings.

First Embodiment

Figure 1:
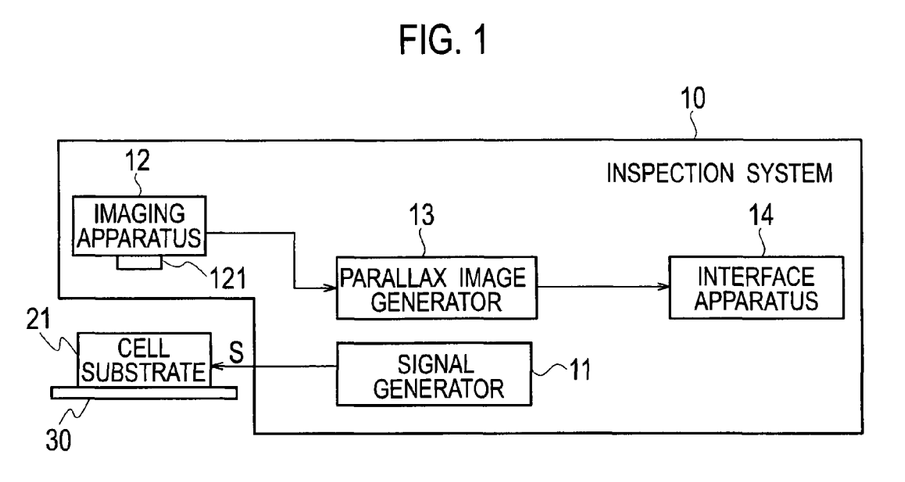
FIG. 1 is a schematic block diagram showing a configuration of an inspection system according to a first embodiment.

A cell substrate inspection system 10 according to the first embodiment shown in FIG. 1 is a system of inspecting a cell substrate 21 for use in an integral-imaging 3D image display apparatus. The cell substrate 21 is a planar display substrate which is bonded to a lenticular lens for use and, as later described, includes a display region composed of an array of plural sub-regions. Each sub-region displays parallax image information obtained by dividing each of plural parallax images.

The inspection system 10 includes a signal generator 11, an imaging apparatus 12, a parallax image generator 13, and an interface apparatus 14. The signal generator 11 sends a display signal S causing the cell substrate 21 as an inspection object, to display a test image. The imaging apparatus 12 captures an image of the test image displayed on the cell substrate 21 receiving the display signal S. The parallax image generator 13 generates a parallax image prediction of each parallax image which can be obtained when the cell substrate 21 is bonded to a lenticular lens by arranging sets of parallax image information of the captured test image for each parallax image. The interface apparatus 14 displays the parallax image predictions.

Before explanation of the method of using the inspection system 10 shown in FIG. 1 to inspect the cell substrate 21, the structure of the integral-imaging 3D image display apparatus 20 is described with reference to FIG. 2. The 3D image display apparatus 20 has a structure in which the cell substrate 21 displaying images is bonded to a lens plate 22 including a lenticular lens 221 with an adhesive 23.

The cell substrate 21 includes a laminate structure of first and second substrates 212 and 213. Within the cell substrate 21, plural pixels are arranged in a predetermined pattern, for example, in a matrix fashion. First and second polarization plates 211 and 214 are provided outside of the first and second substrate 212 and 213, respectively, so as to be opposed to each other.

The first substrate 212 is a rectangular glass substrate, for example. In the surface of the first substrate 212 facing the second substrate 213, a plurality of pixel electrodes (not shown), electrical wires for setting potentials of the pixel electrodes (not shown), and the like are arranged. The pixel electrodes are arranged in a dot fashion in each pixel, and the electrical wires are arranged in a matrix fashion.

The second substrate 213 is a rectangular glass substrate, for example. In the surface of the second substrate 213 facing the first substrate 212, a color filter F, a counter electrode as a common electrode (not shown), and the like are arranged. The color filter F is composed of plural color layers (for example, red, green, and blue layers) arranged in a dotted or a striped fashion and a light shielding layer such as a black matrix.

If the cell substrate 21 is a liquid crystal panel, a not-shown backlight is provided under the cell substrate 21.

The lens plate 22 has a structure including a protective glass 222 and a lenticular lens 221 which are laid on each other. The lenticular lens 221 includes plural cylindrical lenses side by side in a direction (in a short-side direction) perpendicular to the axial direction (the longitudinal direction, or the ridge line direction) thereof. Each cylindrical lens has a shape obtained by dividing a column into two in the axial direction. The cylindrical lens has a curvature on one side and includes one light bending surface. The lenticular lens 221 includes plural barrel-shaped cylindrical lenses arranged side by side, and curve surfaces T of the cylindrical lenses face the cell substrate 21. Light emitted from the display region of the cell substrate 21 is incident to the lenticular lens 221 through the curve surfaces T, then passes through the lenticular lens 221 and protective glass 222, and then outputted to the outside of the 3D image display apparatus 20.

The adhesive 23 is provided between the second substrate 213 and protective glass 222 around the lenticular lens 221 to bond the cell substrate 21 and lens plate 22. The adhesive 23 is formed between the cell substrate 21 and lens plate 22 into a rectangular frame shape, for example. The adhesive 23 can be light curing resin.

Figure 3:
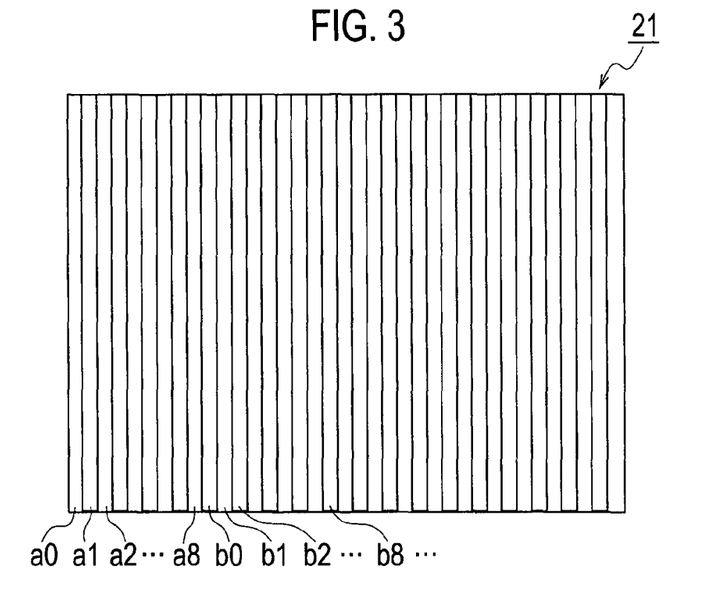
FIG. 3 is a top view schematically showing a display region of a cell substrate of the three-dimensional image display apparatus shown in FIG. 2.

Next, a description is given of the display region of the cell substrate 21 with reference to FIG. 3. FIG. 3 shows an example of the display region of the cell substrate 21 when the number of parallax images is nine. The display region of the cell substrate 21 is divided into sub-regions displaying the nine parallax images 0 to 8. The number of parallax images is not limited to nine.

As shown in FIG. 3, the display region of the cell substrate 21 is divided into stripe sub-regions a0 to a8, b0 to b8 . . . extending in a column direction. Each of the sub-regions a0, b0 . . . displays parallax image information of each portion obtained by dividing the parallax image 0. Furthermore, the sub-regions a1, b1 . . . display parallax image information of each portion obtained by dividing the parallax image 1. Similarly, sets of parallax image information of the portions of the parallax images 2 to 8 are displayed in the sub-regions a2, b2 . . . a3, b3 . . . and a8, b8 . . . . In short, in the display region of the cell substrate 21, the sets of parallax image information of the parallax images 0 to 8 are displayed side by side in turn in the row direction.

Figure 2:
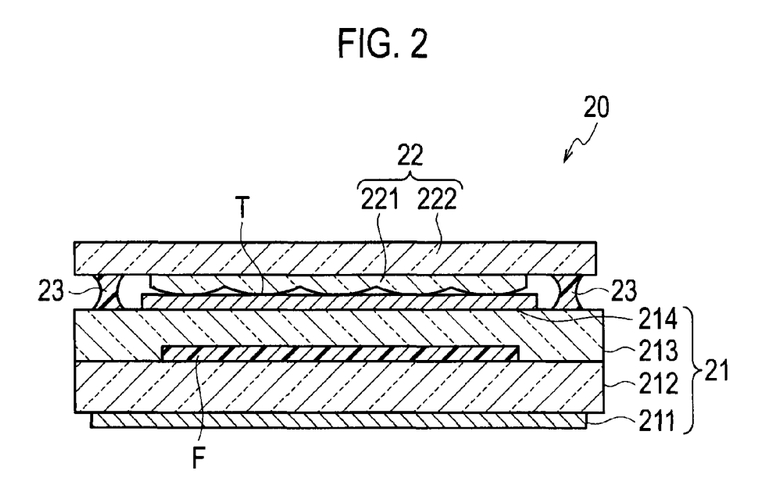
FIG. 2 is a cross-sectional view schematically showing an example of a three-dimensional image display apparatus.
Figure 4:
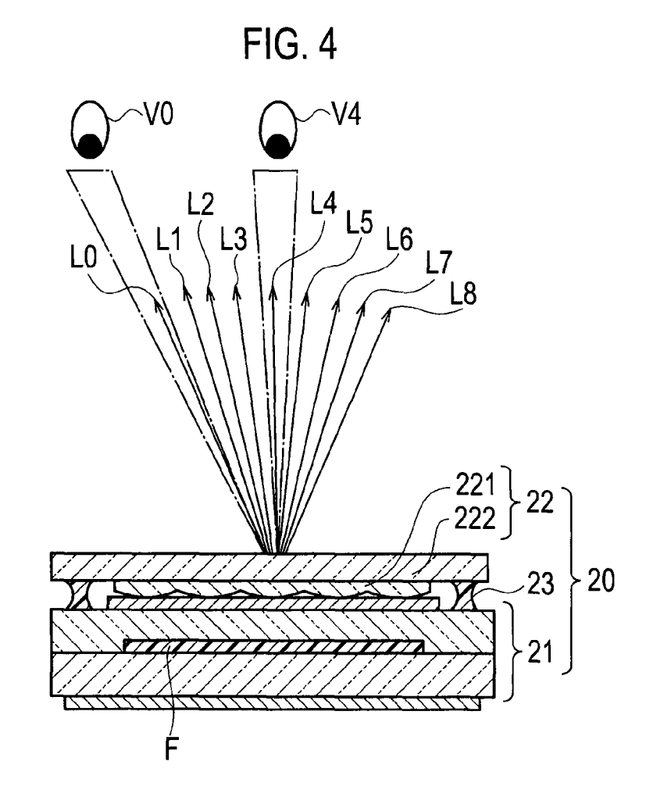
FIG. 4 is a schematic view showing a principle of stereoscopic display by the three-dimensional image display apparatus shown in FIG. 2.

FIG. 4 shows the principle of stereoscopic display by the 3D image display apparatus 20 shown in FIG. 2. Rays of light emitted from the display region of the cell substrate 21 are radiated by the lenticular lens 221 in predetermined directions defined for the individual parallax images. In FIG. 4, arrows L0 to L8 indicate directions of the sets of parallax image information of the parallax images 0 to 8 radiated from the cell substrate 21, respectively.

The sets of parallax image information of the parallax image 0 radiated in the same direction are arranged side by side to form the parallax image 0. In a similar manner, the sets of parallax image information of the parallax images 1 to 8 are arranged side by side for each parallax image to form the parallax images 1 to 8, respectively. When the 3D image display apparatus 20 is observed in a predetermined direction, therefore, one of the parallax images 0 to 8 is observed. For example, the parallax image 0 is observed at a viewing point V0 of FIG. 4, and the parallax image 4 is observed at a viewing point V4.

As described above, the 3D image display apparatus 20 uses the cell substrate 21 and lenticular lens 221 to display plural parallax images (two-dimensional images), which look in a little different ways depending on the viewing angles, thus forming a 3D image. In other words, the 3D image display apparatus 20 displays a stereoscopic image by displaying parallax images taken in the plural directions according to the viewing angles.

Next, a description is given of inspection of the cell substrate 21. The cell substrate 21 is inspected for the presence of bright and dark dot defects, linear defects, display unevenness, and the like. The bright dot defect refers to a dot always bright in the display region of the cell substrate 21 independent of the display signal S prescribing the display image on the cell substrate 21, and the dark dot defect is a dot always dark in a similar manner. The linear defect includes bright or dark dots successively located from end to end of the display region. As for the bright and dark dot defects, the presence of a bright or dark dot defect solely caused does not always result in determination that the cell substrate 21 is defective. For example, in the case of a successive dark dot defect including plural dark dots successively located or a successive bright dot defect including plural bright dot defects successively located, it is defined how many dark or bright dot defects are considered as a successive dark or bright dot defect which is an object determined to be defective. Furthermore, it is defined by how many defined successive dark or bright dot defects the cell substrate 21 is determined to be defective. The aforementioned criteria are set to determine whether the cell substrate 21 is a non-defective product. This is because even if there is one independent dark or bright dot defect, the viewer of the display image of the 3D image display apparatus 20 often does not notice the dark or bright dot defect or are not bothered by the same. The cell substrate 21 including a dark or bright dot defect can be shipped as a non-defective product in some cases.

If the cell substrate 21 is defective, it is necessary to examine how each parallax image looks. It is not proper that the quality of the cell substrate 21 is determined only by the results of inspection for dark or bright dot defects in the display region of the cell substrate 21. This is because inspection for dark or bright dot defects is necessary for each parallax image obtained through the lenticular lens 221 bonded to the cell substrate 21. In other words, it is necessary to know the influence of defects of the cell substrate 21 on each parallax image.

Using the test image which is displayed on the cell substrate 21 and is then captured by the imaging apparatus 12, the parallax image generator 13 predicts parallax images which could be obtained by arranging the sets of parallax image information of the test image side by side when the cell substrate 21 is bonded to the lenticular lens 221. The test image captured by the imaging apparatus 12 includes the sets of parallax image information of each parallax image which are arranged in turn. The parallax image generator 13 extracts the regions corresponding to each viewing point from the captured test image to generate a parallax image prediction of each parallax image. To be specific, every n-th sub-regions (n is the number of parallax images) are extracted from the display region of the cell substrate 21, and the sets of parallax image information displayed in the extracted sub-regions are then arranged side by side to generate a parallax image prediction of each parallax image. For example, when the test image includes the parallax images 0 to 8, the sets of parallax image information displayed in every n-th sub-regions extracted from the display region of the cell substrate 21 are arranged to generate parallax image predictions 0p to 8p of the parallax images 0 to 8.

Figure 5:
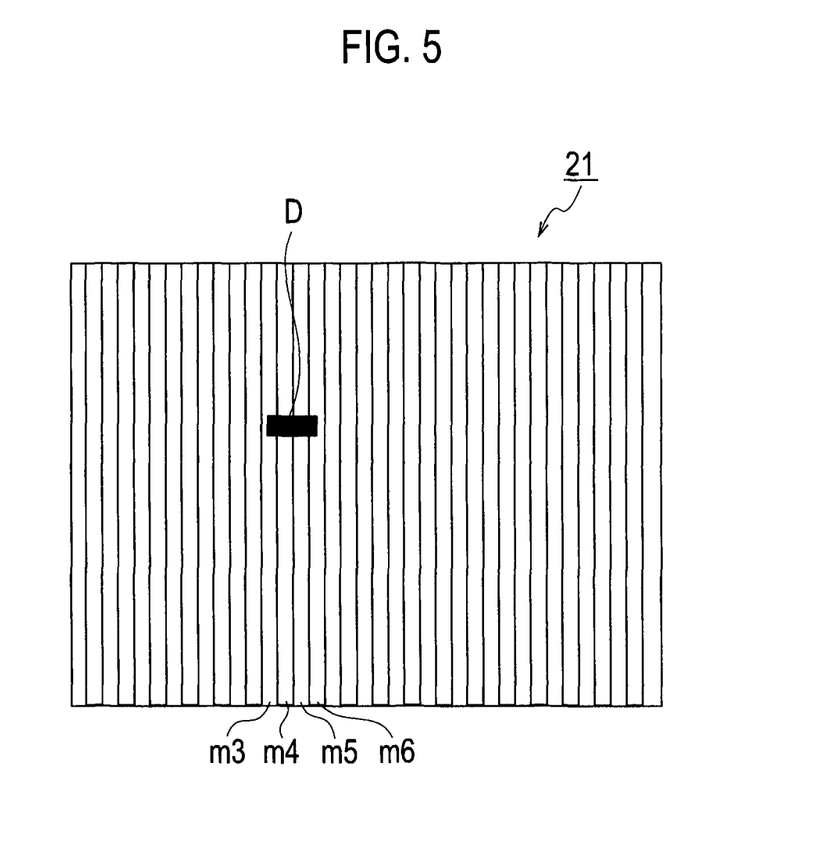
FIG. 5 is a top view schematically showing an example of a cell substrate having a defect in the display region.
Figure 6A:
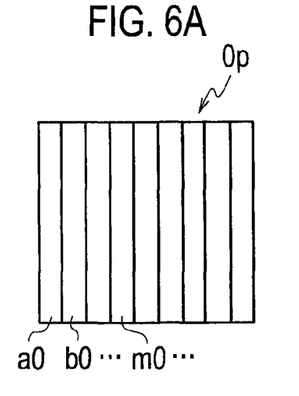
FIGS. 6A to 6I are schematic views showing examples of parallax image predictions generated by the inspection system according to the first embodiment.
Figure 6B:
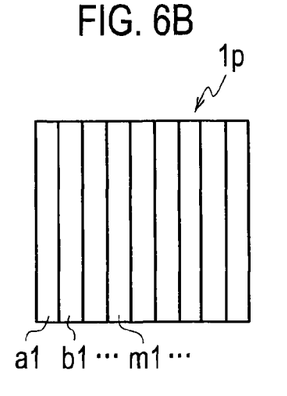
Figure 6C:
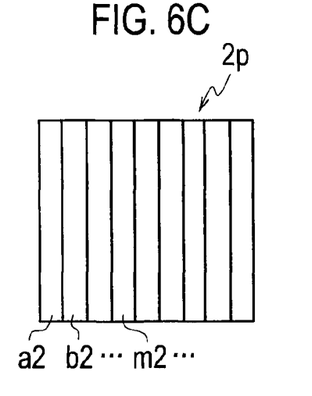
Figure 6D:
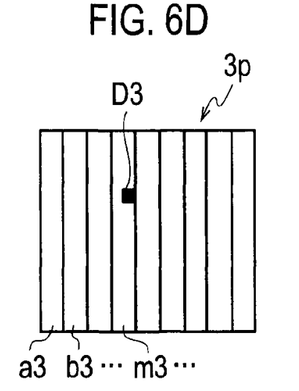
Figure 6E:
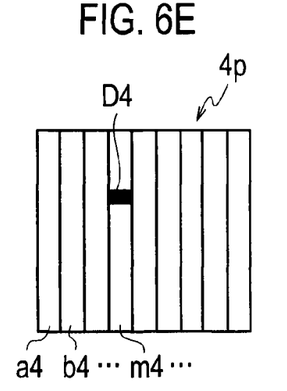
Figure 6F:
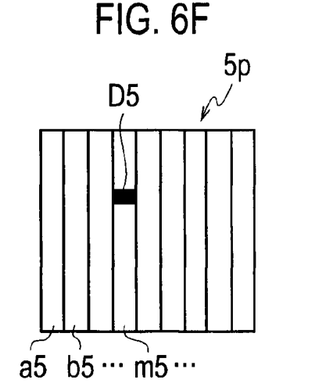
Figure 6G:
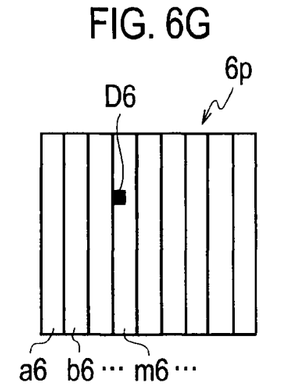
Figure 6H:
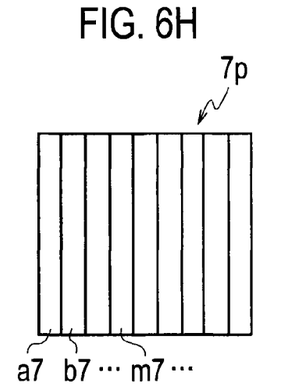
Figure 6I:
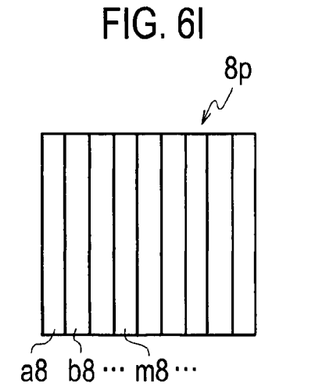

Hereinafter, a description is given of an example of the method of inspecting the cell substrate 21 when the display region includes a defect shown in FIG. 5. FIG. 5 shows an example in which a defect D including a series of dark dot defects from the sub-region m3 to the sub-region m6 in the cell substrate 21.

FIGS. 6A to 6I show the parallax image predictions 0p to 8p of the parallax images 0 to 8 which will be obtained when the cell substrate 21 shown in FIG. 5 is bonded to the lenticular lens 221. As already described, the parallax image predictions 0p to 8p are obtained by arranging the sets of parallax image information of each parallax image of the test image side by side. The defect D of the cell substrate 21 shown in FIG. 5 is caused in the regions m3 to m6 which display part of the parallax image information of the parallax images 3 to 6, respectively. Accordingly, as shown in FIG. 6A to 6I, the parallax image predictions 3p to 6p includes defects D3 to D6, respectively. According to the inspection system 10 shown in FIG. 1, it is therefore possible to know the influence of defects included in the cell substrate 21 on each parallax image.

Figure 7:
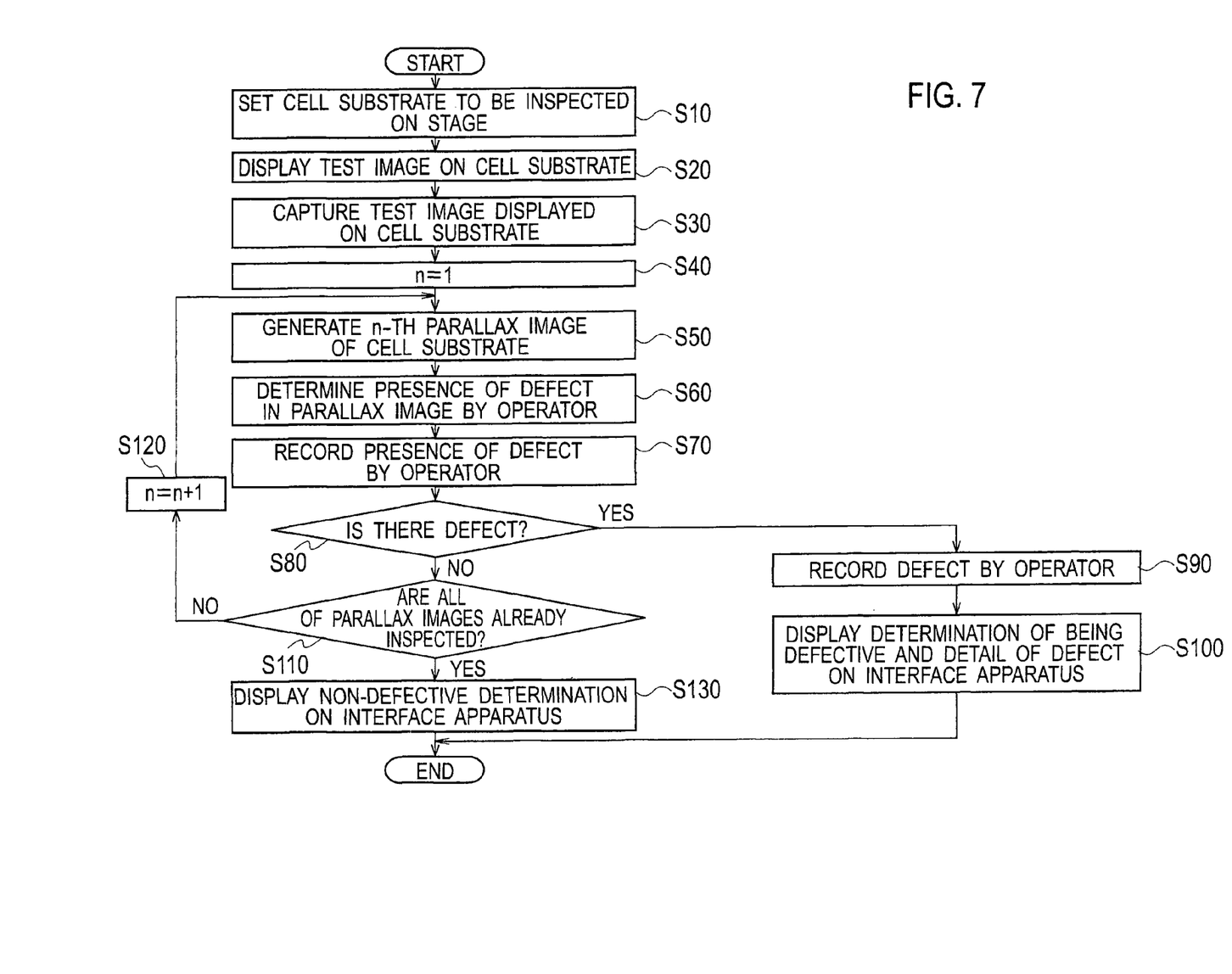
FIG. 7 is a flowchart for explaining an inspection method by the inspection system according to the first embodiment.

With reference to the flowchart of FIG. 7, a description is given of an example of the method of inspecting the cell substrate 21 by using the inspection system 10 shown in FIG. 1.

i) In step S10 of FIG. 7, the cell substrate 21 to be inspected is placed on a stage 30.

ii) In step S20, the signal generator 11 generates the display signal S causing the cell substrate 21 to display a test image. The cell substrate 21 receives the display signal S and displays the test image. For example, in the case of inspection for a dark dot defect, the signal generator 11 sends to the cell substrate 21 the display signal S causing all the pixels to have maximum brightness. In such a case, the display region of the cell substrate 21 is visually observed as a white screen although zooming-in shows that each R, G, or B pixel has the maximum brightness. Furthermore, in the case of inspection for a bright dot defect, the signal generator 11 sends to the cell substrate 21 the display signal S causing all the pixels to have the minimum brightness.

iii) In step S30, the imaging apparatus 12 captures the test image displayed on the cell substrate 21. The optical system including the imaging apparatus 12 and an imaging lens 121 used in the imaging apparatus 12 needs a resolution high enough to determine the state of each R, G, or B pixel (hereinafter, referred to as a sub-pixel). If the states of all the sub-pixels of the cell substrate 21 cannot be determined by one shot due to the relation between the resolution of the imaging apparatus 12 and the number of pixels of the cell substrate 21, it is possible to capture the test image several times while moving a smaller imaging range.

(iv) In step S40, a number of the parallax image of which the parallax image prediction is generated at first is set to 1. For example, when the test image includes nine parallax images 0 to 8 and parallax image predictions of the parallax images 0 to 8 are generated according to n=1 to 9, by setting n=1, a parallax image prediction of the parallax image 0 is generated at first.

(v) In step S50, the parallax image generator 13 performs data processing for the captured image of the test image to generate a parallax image prediction of the number n. To be specific, the sets of parallax image information of the parallax image No. n included in the test image are arranged side by side to generate a parallax image prediction. The generated parallax image prediction is displayed on the interface apparatus 14.

(vi) In step S60, an operator who is using the inspection system 10 observes the parallax image predictions displayed on the interface apparatus 14 and determines the presence of a defect in each parallax image based on the parallax image predictions. Specifically, the operator determines the quality of the cell substrate 21 based on the number of dark or bright dot defects in a successive dark or bright dot defect which is defined as an object for quality determination of the cell substrate 21 and the allowable number of successive dark or bright dot defects. For example, it is assumed that a successive dark or bright dot defect including three or more dark or bright dot defects is defined as a defect which is an object for the quality determination of the cell substrate 21. The cell substrate 21 is determined to be a defective if the number of successive dark or bright dot defects is greater than the allowable number. Furthermore, the quality of the cell substrate 21 may be determined based on the presence of a linear defect or display unevenness.

(vi) In step S70, based on the observation of the parallax image predictions, the operator records the presence of a defect in the cell substrate 21. For example, the operator inputs the presence of a defect in the cell substrate 21 to the interface apparatus 14. The information inputted to the interface apparatus 14 is recorded in the inspection system 10 as a determination result. If the cell substrate 21 includes a defect in the step S80, the process proceeds to step S90, and the operator records the detail of the defect. For example, the operator inputs the detail of the defect to the interface apparatus 14. In step S100, the interface apparatus 14 displays that the cell substrate 21 is determined to be a defective and the detail of the defect. The process is then terminated.

vii) On the other hand, if the cell substrate 21 is not defective in the step S80, the process proceeds to step S110, in which it is determined whether all of the parallax images of the cell substrate 21 are already inspected. If all of the parallax images are not yet inspected, in the step S120, the number n of the parallax image to be predicted is incremented by 1, and the process returns to the step S50. For example, after the parallax image 0 is inspected for defects at n=1, the parallax image 1 is inspected for defects at n=2. When the inspection for all the parallax images is finished, the process proceeds to step S130, and the interface apparatus 14 displays that the cell substrate 21 is determined to be a non-defective product.

In the above example, if it is determined that a certain one of the parallax images is defective, the cell substrate 21 is determined to be defective without performing the inspection for defects in the parallax images not yet inspected, and the process is terminated. However, as described later, such a defective cell substrate 21 can be used to manufacture the three-dimensional image display apparatus 20 in some cases depending on the position of the defect in the cell substrate 21 and the quality criteria. Accordingly, all of the parallax images of the cell substrate 21 may be inspected independently of the presence of a defect in each parallax image before the process is terminated.

The way of outputting the result of the quality determination can be displaying the results on various types of display apparatuses, outputting the results through a printer, or recording the results in a database integrally managing quality data of the cell substrate 21. For example, the result of quality determination of the cell substrate 21 is inputted to the interface apparatus 14 and is then transmitted from the inspection system 10 to the database.

The method of clarifying sub-pixels of a parallax image of which the parallax image prediction is to be generated can be, in addition to the method of simultaneously displaying all the parallax images on the cell substrate 21, a method of displaying a test image including only one selected from the plural parallax images. For example, it is possible to display only pixels of a particular parallax image with a determination brightness while displaying pixels of the other parallax images with a brightness different from the determination brightness. In the inspection for dark dot defects, only the sub-pixels of a parallax image wanted to be predicted are displayed with the maximum brightness while the sub-pixels of the other parallax images are displayed with the minimum brightness.

The aforementioned method of displaying the test image including only a particular parallax image is also effective when the parallax image cannot be specified if all the parallax images are simultaneously displayed. For example, when the parallax image is specified by how many sub-regions there are before the referential position of the cell substrate 21 (for example, the left end of the display region), if a linear defect is caused at the referential position of the cell substrate 21, the referential position can be misidentified, preventing precise specification of the parallax image. However, if the parallax images are sequentially inspected one by one, it is possible to precisely recognize which place is influenced by defects caused in the cell substrate 21.

Furthermore, in the inspection for bright dot defects, which is performed by making dark the entire display region of the cell substrate 21, the positions of sub-pixels cannot be specified in some cases due to little light emitted from good sub-pixels. To cope with such a problem, the positions of sub-pixels in the imaging range of the imaging apparatus 12 are recorded in advance using a maximum brightness image for the dark dot inspection.

Specifically, first, the maximum brightness image with each R, G, or B pixel of the cell substrate 21 having the maximum brightness is captured by the imaging apparatus 12, and each position of the sub-pixels at this time is recorded. Subsequently, the test image for the bright dot inspection is displayed on the cell substrate 21 and is then captured. Comparing the recorded positions of the sub-pixels with the captured test image, the positions of sub-pixels in the test image can be specified.

Unlike the inspection method of the first embodiment, it is possible to perform inspections for successive dark or bright dot defects of each parallax image after the process of bonding the cell substrate 21 to the lenticular lens 221. However, in such a case, even if the cell substrate 21 is defective, the whole 3D image display apparatus 20 including the lenticular lens 221 should be disposed of. Alternatively, the 3D image display apparatus 20 is dissembled, and only the cell substrate 21 is disposed of. The lenticular lens 221 is bonded to another cell substrate 21 again. However, this will increase the manufacturing cost and time of the 3D image display apparatus 20.

On the other hand, according to the method of inspecting the cell substrate 21 of the first embodiment, the substrate 21 can be solely inspected for successive dark or bright dot defects in each parallax image before the process of bonding the cell substrate 21 to the lenticular lens 221. This can prevent the manufacturing cost and time of the 3D image display apparatus 20 from increasing.

As described above, according to the inspection system 10 of the first embodiment, based on the display image on the cell substrate 21 before the cell substrate 21 is bonded to the lenticular lens 21, it is predicted how each parallax image looks when the cell substrate 21 is bonded to the lenticular lens 21. By determining the presence of a defect in the predicted parallax images, the presence of a defect in the cell substrate 21 influencing each parallax image can be examined before the cell substrate 21 is bonded to the lenticular lens 221. It is therefore possible to provide the inspection system and method which detect defects in the cell substrate 21 for use in the 3D image display apparatus 20 while preventing the manufacturing cost and time thereof from increasing.

Next, a description is given of a method of manufacturing the 3D image display apparatus 20, the method more effectively utilizing the result of inspection of the cell substrate 21.

Even if the same cell substrate 21 is used, the successive dark or bright dot defects occur in different ways in the 3D image display apparatuses 20 using different numbers of parallax images. Accordingly, in some cases, the cell substrate 21 which is determined to be defective for the 3D image display apparatus 20 using a certain number of parallax images can be applied to another 3D image display apparatus 20 using a different number of parallax images without any problem. As described below, by obtaining the result of inspection of the cell substrate 21 before the cell substrate 21 is bonded to the lenticular lens 221, the number of parallax images of the 3D image display apparatus 20 to which the defective cell substrate 21 can be applied as a non-defective product can be determined based on the result of inspection of the cell substrate 21, thus manufacturing the 3D image display apparatus 20.

Figure 8:
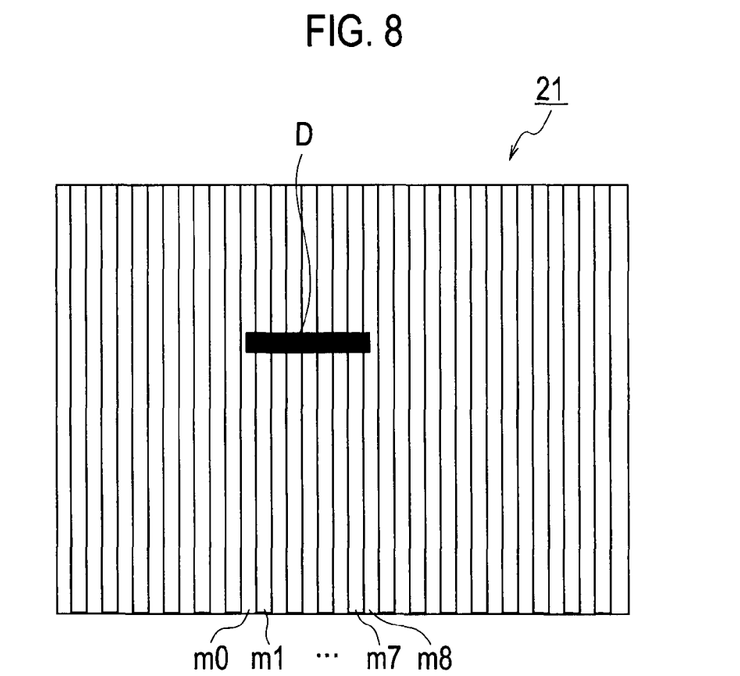
FIG. 8 is a top view schematically showing an example of defects caused in the cell substrate.

For example, as shown in FIG. 8, it is assumed that a defect D is caused successively from the region m0 to the region m8 in the cell substrate 21. If the cell substrate 21 shown in FIG. 8 is applied to the 3D image display apparatus 20 using seven parallax images, the defective regions m0 and m7 are included in a same parallax image (the parallax image 0), and the defective regions m1 and m8 are included in a same parallax image (the parallax image 1). In the parallax images 0 and 1, the defective sets of parallax image information are located side by side. When the quality criteria of the cell substrate 21 are defined so that the cell substrate 21 is determined to be defective when the cell substrate 21 includes two or more successive dark or bright dot defects, the cell substrate 21 shown in FIG. 8 is determined to be defective.

However, in the 3D image display apparatus 20 using nine parallax images, each of the parallax images includes each defect due to the defect D of the cell substrate 21 shown in FIG. 8 but does not include successive defects. Accordingly, the cell substrate 21 shown in FIG. 8 is determined to be a non-defective.

By inspecting the cell substrate 21 shown in FIG. 8 for defects before the cell substrate 21 is bonded to the lenticular lens 221, it can be determined that the cell substrate 21 is to be applied to not the 3D image display apparatus 20 using seven parallax images but the 3D image display apparatus 20 using nine parallax images. This can prevent occurrence of defectives.

Figure 9:
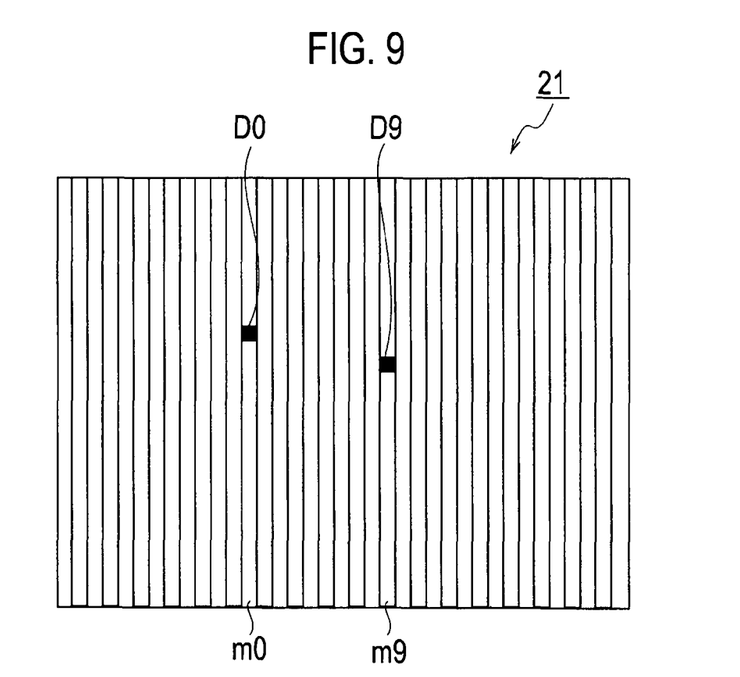
FIG. 9 is a top view schematically showing another example of defects caused in the cell substrate.

Moreover, it is assumed that defects D0 and D9 are caused in the regions m0 and m9 in the cell substrate 21 as shown in FIG. 9. When the cell substrate 21 shown in FIG. 9 is applied to the 3D image display apparatus 20 using nine parallax images, the defective regions m0 and m9 are included in a same parallax image, in which the defects are located side by side. In short, the defect of the cell substrate 21 shown in FIG. 9 greatly influences the image displayed by the 3D image display apparatus 20 using nine parallax images.

On the other hand, when the cell substrate 21 shown in FIG. 9 is applied to the 3D image display apparatus 20 using seven parallax images, the defective regions m0 and m9 are included in different parallax images. Accordingly, the defect of the cell substrate 21 shown in FIG. 9 little influences the image displayed by the 3D image display apparatus 20 using seven parallax images.

Accordingly, before the cell substrate 21 is bonded to the lenticular lens 221, it can be determined that the cell substrate 21 which is defective for the 3D image display apparatus 20 using nine parallax images is to be applied to the 3D image display apparatus 20 using seven parallax images. This can prevent occurrence of defectives.

As described above, based on the result of inspection of the cell substrate 21 which is obtained before the cell substrate 21 is bonded to the lenticular lens 221 and the quality criteria set for each parallax image of the 3D image display apparatus 20, the number of parallax images is determined so that each parallax image satisfies the quality criteria when the cell substrate 21 is used. The inspected cell substrate 21 is bonded to the lenticular lens 221 to manufacture the 3D image display apparatus 20 using the determined number of parallax images. It is therefore possible to manufacture the 3D image display apparatus 20 with no defect using the defective cell substrate 21. This can prevents the manufacturing cost and time of the 3D image display apparatus 20 from increasing.

Furthermore, as described below, the position of the cell substrate 21 where the lenticular lens 221 is to be bonded is adjusted according to the result of inspection of the cell substrate 21. The defective cell substrate 21 can be used to manufacture of the 3D image display apparatus 20 less influenced by the defect of the cell substrate 21.

In the 3D image display apparatus 20, defects of the parallax image viewable when the screen of the 3D image display apparatus 20 is seen from the front around the center (hereinafter, referred to as a central parallax image) are the biggest problem. This is because the central parallax image is a front image representing the front surface of an object seen from the front in many cases. The central parallax image showing the front image of the object is the most prominent for people who are seeing the image displayed by the 3D image display apparatus 20. The central parallax image is normally transmitted through central part of each cylindrical lens constituting the lenticular lens 221.

At manufacturing the 3D image display apparatus 20 less influenced by defects of the cell substrate 21, it is effective that the cell substrate 21 and the lenticular lens 221 are bonded to each other so that the parallax image least influenced by defects of the cell substrate 21 is the central parallax image. In other words, by bonding the cell substrate 21 to the lenticular lens 221 at the position displaced from the position previously set, parallax images greatly influenced by defects of the cell substrate 21 are located at obscure places in the image displayed by the 3D image display apparatus 20.

The cell substrate 21 is bonded to the lenticular lens 221 at the position previously set according to the order of the positions of the parallax images to be displayed on the cell substrate 21. Specifically, the position in the lenticular lens 221 where the cell substrate 21 is bonded is set so that the sub-regions of the cell substrate 21 displaying a parallax image wanted to be displayed as the central parallax image will face individual central portions of the cylindrical lenses.

Accordingly, even if the cell substrate 21 is just displaced from the previously set position to be bonded to the lenticular lens 221 so that the parallax images least influenced by defects of the cell substrate 21 become the central parallax images, the desired parallax image is not displayed as the central parallax image. It is necessary to change the order of the positions of the parallax images to be displayed on the cell substrate 21 so that the desired parallax image is displayed as the central parallax image according to the displacement of the position of the lenticular lens 221 where the cell substrate 21 is bonded.

Figure 10A:
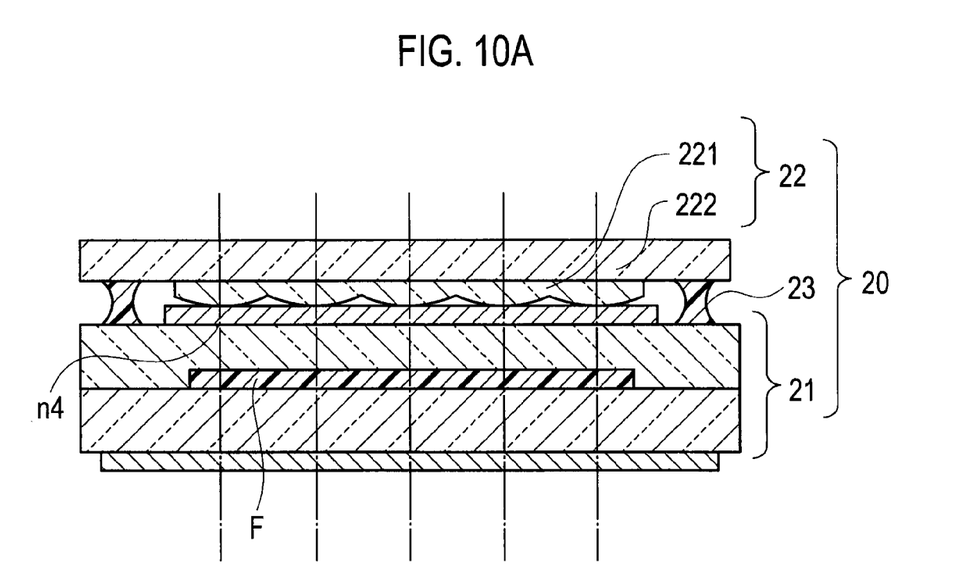
FIGS. 10A and 10B are schematic views illustrating a method of manufacturing a three-dimensional image display apparatus using the result of inspection of a cell substrate.

For example, in the 3D image display apparatus 20 using nine parallax images, it is assumed that the parallax image 4 is displayed as the central parallax image. At this time, as shown in FIG. 10, when the cell substrate 21 is bonded to the lenticular lens 221 at the predetermined set position, the region n4 of the cell substrate 21 displaying a part of the parallax image 4 faces around the central part of one of cylindrical lenses.

Figure 10B:
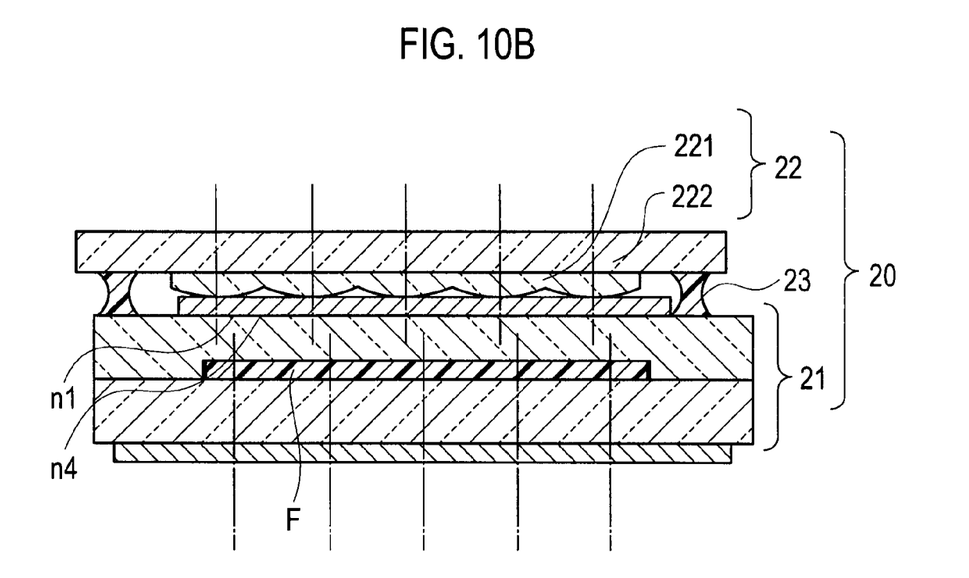

Herein, if a defect is detected in the region n4 of the cell substrate 21 which is originally planed to display the parallax image information of the parallax image 4, the cell substrate 21 is bonded to the lenticular lens 221 so that the region n4 does not face any central part of the cylindrical lenses. For example, when there is no defect in the region n1 which is planned to display the parallax image information of the parallax image 1, as shown in FIG. 10B, the cell substrate 21 is bonded to the lenticular lens 221 so that the region n1 of the cell substrate 21 faces the central part of one of the cylindrical lenses. However, in order to display the parallax image 4 as the central parallax image, the order of the parallax images to be displayed on the cell substrate 21 is changed so that the parallax image 4, which is planned to be displayed in the region n4, is displayed in the region n1. The display control apparatus (not shown), which is configured to set an image to be displayed in each region of the cell substrate 21, is controlled to adjust the parallax image to be displayed in each sub-region of the cell substrate 21. For example, in order to display the parallax image 4 in the region n1 as described above, the parallax images to be displayed on the cell substrate 21 are shifted by three sub-regions. The sets of parallax image information of divisions of each of the parallax images 3 to 8 and 0 to 2 are displayed in the regions a0 to a8, b0 to b8, . . . , n0 to n8 . . . .

As described above, by utilizing the result of inspection of the cell substrate 21 which is obtained before the cell substrate 21 is bonded to the lenticular lens 221, it is possible to reduce the influence of defects of the cell substrate 21 on an image displayed by the 3D image display apparatus 20.

Specifically, the cell substrate 21 is bonded to the lenticular lens 221 based on the result of inspection of the cell substrate 21 so that the parallax image least influenced by the defect of the cell substrate 21 is located around the central part of the display image of the 3D image display apparatus 20. Furthermore, the order of the parallax images to be displayed on the cell substrate 21 is changed so that the parallax image least influenced by the defect of the cell substrate 21 is set as the parallax image located around central part of the display image of the 3D image display apparatus 20. This can reduce the influence of the defect of the cell substrate 21 on the display image of the 3D image display apparatus 20 that people is seeing. It is therefore possible to manufacture the 3D image display apparatus 20 using the defective cell substrate 21, thus preventing the manufacturing cost and time of the 3D image display apparatus 20 from increasing.

Second Embodiment

Figure 11:
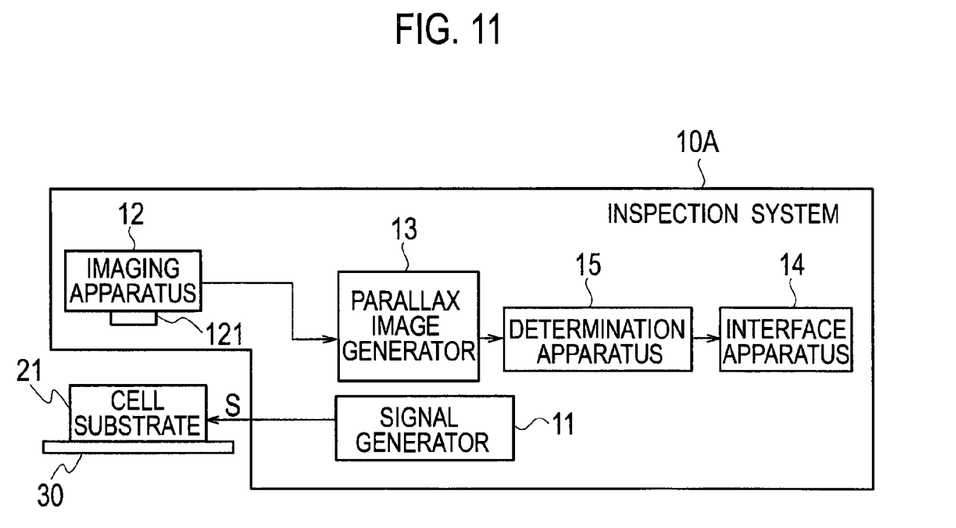
FIG. 11 is a schematic block diagram showing a configuration of an inspection system according to a second embodiment.

An inspection system 10A according to a second embodiment differs from the inspection system 10 shown in FIG. 1 in further including a determination apparatus 15 as shown in FIG. 11. The determination apparatus 15 analyses the parallax image predictions to determine the presence of a defect of the cell substrate 21. The other configuration is the same as that of the first embodiment shown in FIG. 1.

The determination apparatus 15 includes, as the quality criteria, definitions of defects which are used to determine the quality of the cell substrate 21, such as the number of dark or bright dots included in the successive dark or bright dot defects, allowable numbers of successive dark or bright dot defects, and the like.

Figure 12:
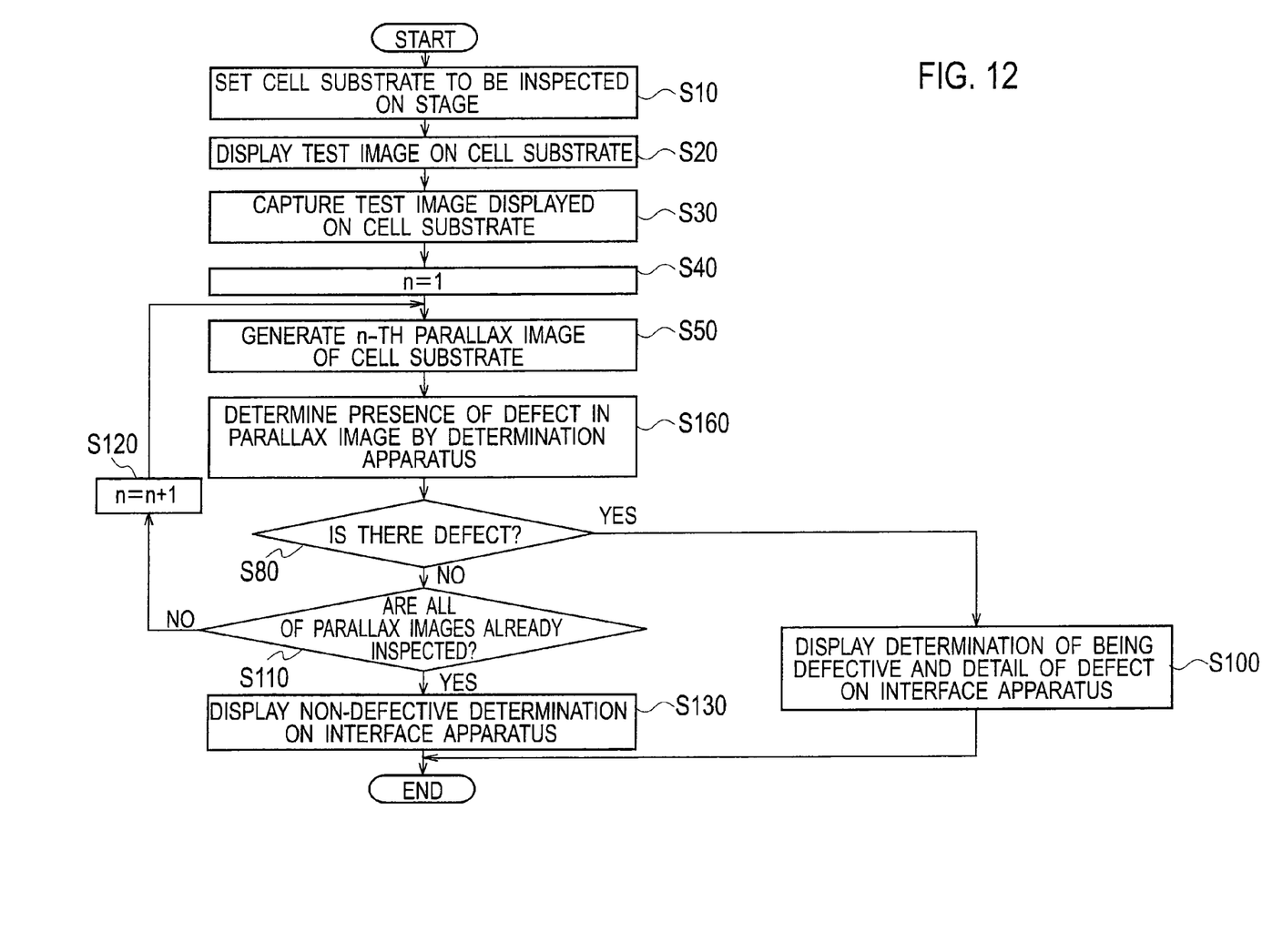
FIG. 12 is a flowchart for explaining an inspection method by the inspection system according to the second embodiment.

The inspection method by the inspection system 10A shown in FIG. 11 is basically the same as that of the first embodiment as shown in the flowchart of FIG. 12 but differs in including step S160 of the flowchart of FIG. 12 instead of the step 60 of the flowchart shown in FIG. 7. In the step 60, the operator visually determines the presence of a defect in each parallax image based on the parallax image predictions. In contrast, in the step S160 of the flowchart shown in FIG. 12, the determination apparatus 15 automatically determines the presence of a defect in the cell substrate 21. Moreover, in the steps S70 and S90 of the flowchart shown in FIG. 7, the operator records the presence of the defect and the detail thereof manually. In the method of the second embodiment, the presence and detail of defects are automatically recorded in the inspection system 10A.

Hereinafter, a description is given of an example of the method of inspecting the cell substrate 21 using the inspection system 10A shown in FIG. 11 with reference to the flowchart of FIG. 12.

i) In steps S10 to S50 of the flowchart shown in FIG. 12, the test image displayed on the cell substrate 21 to be inspected is captured, and the sets of parallax image information of the parallax image No. n included in the test image are arranged side by side to generate a parallax image prediction.

ii) In the step S160, the determination apparatus 15 analyses the parallax image prediction generated for the cell substrate 21 and detects a defect defined as the object of the quality determination. The determination apparatus 15 compares the defect detected in the parallax image prediction of the cell substrate 21 with the set determination criterion to determine the presence of a defect of the cell substrate 21. If the number of detected defects is not more than the determination criterion, for example, the cell substrate 21 is determined to be not-defective in the step S80. On the other hand, if the number of detected defects is more than the determination criterion, the cell substrate 21 is determined to be defective in the step S80.

iii) If the cell substrate 21 includes a defect, the process proceeds to the step S100, and the interface apparatus 14 displays the detail of the defect and displays that the cell substrate 21 is determined as a defective product. The process is then terminated. On the other hand, if the cell substrate 21 does not include a defect, the process proceeds to the step S110, and it is determined whether all of the parallax images of the cell substrate 21 are already inspected. If all of the parallax images are not yet inspected, the process proceeds to the step S50, and the uninspected parallax images undergo the inspection. If all of the parallax images are already inspected, the process proceeds to the step S130, and the interface apparatus 14 displays that the cell substrate 21 is determined to be a non-defective product.

Furthermore, the interface apparatus 14 may display the position of the defective part of the parallax image prediction which is determined to be defective by the determination apparatus 15, the image of the cell substrate 21 captured by the imaging apparatus 12, the parallax image predictions generated by the parallax image generator 13, and the like.

The method of automatically determining the quality, which is described in the second embodiment, has an advantage of performing stable inspection in a short time without labor. On the other hand, the method of determining the quality by an operator, which is described in the first embodiment, flexibly responds to changes in inspection contents and can easily cope with an inspection which is difficult to qualify, such as an inspection of display unevenness.

As described above, according to the inspection system 10A of the second embodiment, it is possible to automatically determine whether the cell substrate 21 is defective before the cell substrate 21 is bonded to the lenticular lens 221.

It is therefore possible to provide inspection system and method which detect a defect of the cell substrate 21 for use in the 3D image display apparatus 20 while preventing the manufacturing cost and time from increasing. The others are substantially the same as the first embodiment, and the redundant description is omitted.

Similar to the first embodiment, the result of inspection of the cell substrate 21 which is obtained before the cell substrate 21 is bonded to the lenticular lens 221 is used in the method of manufacturing the 3D image display apparatus 20. Accordingly, the cell substrate 21 determined to be defective for the 3D image display apparatus 20 using a certain number of parallax images can be applied to another 3D image display apparatus 20 using a different number of parallax images without any problem in some cases.

For example, based on the result of inspection of the cell substrate 21 which is obtained before the cell substrate 21 is bonded to the lenticular lens 221 and the quality criteria set for each parallax image of the 3D image display apparatus 20, the determination apparatus 15 determines the number of parallax images so that each parallax image satisfies the quality criteria when the cell substrate 21 is used. For example, the number of parallax images is determined so as not to cause successive defects not satisfying the quality criteria in each parallax image. The inspected cell substrate 21 is bonded to the lenticular lens 221 to generate the 3D image display apparatus 20 using the determined number of parallax images.

Moreover, similarly to the first embodiment, based on the result of inspection of the cell substrate 21, the position of the cell substrate 21 where the lenticular lens 221 is bonded is adjusted so that the parallax image least influenced by a defect of the cell substrate 21 is located around the center of the display image of the 3D image display apparatus 20. At this time, the order of the parallax images to be displayed on the cell substrate 21 is changed so that the parallax image least influenced is the parallax image previously set as the central parallax image in the display image of the 3D image display apparatus 20. For example, based on the result of inspection of the cell substrate 21, the determination apparatus 15 calculates the adjustment amount of the bonding position of the cell substrate 21. The determination apparatus 15 changes the order of the parallax images to be displayed on the cell substrate 21 according to the adjustment amount of the bonding position so that the central parallax image is displayed in the sub-regions facing around the center of each cylindrical lens.

As described above, using the result of inspection of the cell substrate 21 not yet bonded to the lenticular lens 221, it is possible to manufacture the 3D image display apparatus 20 of good quality including the defective cell substrate 21. Accordingly, the manufacturing cost and time of the 3D image display apparatus 20 can be therefore prevented from increasing.

Other Embodiments

In the description of the above first and second embodiments, the cell substrate 21 is composed of a liquid crystal panel. However, the cell substrate 21 can be inspected for defects in a similar manner when the cell substrate 21 is a display substrate of another system such as an organic electroluminescence (EL) device, a cathode tube ray, or a plasma display.

Moreover, the first and second embodiments describe about the system and method of inspecting the cell substrate which is bonded to the lenticular lens for use in the integral-imaging 3D image display apparatus. However, the above embodiments are applicable to a cell substrate of a 3D image display apparatus of another system which does not require special glasses.

For example, the system and method of inspecting a cell substrate in the aforementioned embodiments can be applied to a parallax-barrier 3D image display apparatus in which the cell substrate is attached to a plate called a parallax barrier instead of the lenticular lens. The parallax barrier system is a system in which a parallax barrier having stripe openings to shield light in the stripe fashion is provided in front of the display region of the cell substrate in which a plurality of parallax images are divided into vertically elongated sub-regions and are arranged side by side in turn. The openings formed in the parallax barrier are arranged in a same cycle as that of the parallax images, and the width of the openings is the same as the width of each parallax image. According to the system and method of inspecting a cell substrate according to the embodiments, the presence of a defect in the cell substrate can be determined before the cell substrate is attached to the parallax barrier.

Furthermore, as for an active barrier 3D image display apparatus, which uses a switch of liquid crystal or the like to electrically control the presence of the effect of the parallax barrier, thus implementing switching between 2D and 3D image displays, the presence of a defect in the cell substrate for use in the active barrier 3D image display apparatus can be determined by the system and method of inspecting a cell substrate according to the embodiments.

Still furthermore, the presence and absence of the effect of a lenticular lens are electrically switched using a liquid crystal lens or the like. This can implement a 3D image display apparatus capable of switching between 2D and 3D image displays. According to the system and method for inspecting a cell substrate according to the embodiments, it is possible to determine the presence of a defect in the cell substrate for use in such an active-lens 3D image display apparatus.

While certain embodiments have been described, these embodiments have been presented by way of example only, and are not intended to limit the scope of the inventions. Indeed, the novel apparatus described herein may be embodied in a variety of other forms; furthermore, various omissions, substitutions and changes in the form of the apparatus described herein may be made without departing from the spirit of the inventions. The accompanying claims and their equivalents are intended to cover such forms or modifications as would fall within the scope and spirit of the inventions.

What is claimed is:

1. A system for inspecting a cell substrate which is to be bonded to a lenticular lens for use in an integral-imaging three-dimensional image display apparatus and includes a display region having an array of a plurality of sub-regions, each sub-region displaying a set of parallax image information obtained by dividing each of a plurality of parallax images, the system for inspecting the cell substrate comprising:
   a signal generator configured to transmit to the cell substrate a display signal causing the cell substrate as an inspection object to display a test image;
   an imaging apparatus configured to capture the test image displayed on the cell substrate receiving the display signal before bonding the lenticular lens to the cell substrate, the captured test image including a plurality of the set of parallax image information of the parallax images which are arranged in turn;
   a parallax image generator configured to generate a parallax image prediction of the parallax image which can be obtained when the lenticular lens is bonded to the cell substrate by extracting regions corresponding to each viewing point from the captured test image and arranging the set of parallax image information displayed in the extracted regions of the captured test image for each parallax image of the test image displayed on the cell substrate before bonding the lenticular lens to the cell substrate, the parallax image prediction being predicted respectively for each of the parallax images; and
   an interface apparatus configured to display the parallax image prediction.

2. The system of the claim 1, wherein the test image displayed on the cell substrate includes only one parallax image selected from the plurality of parallax images.

3. A system for inspecting a cell substrate which is to be bonded to a lenticular lens for use in an integral-imaging three-dimensional image display apparatus and includes a display region having an array of a plurality of sub-regions, each sub-region displaying a set of parallax image information obtained by dividing each of a plurality of parallax images, the system for inspecting the cell substrate comprising:
   a signal generator configured to transmit to the cell substrate a display signal causing the cell substrate as an inspection object to display a test image;
   an imaging apparatus configured to capture the test image displayed on the cell substrate receiving the display signal before bonding the lenticular lens to the cell substrate, the captured test image including a plurality of the set of parallax image information of the parallax images which are arranged in turn;
   a parallax image generator configured to generate a parallax image prediction of the parallax image which can be obtained when the lenticular lens is bonded to the cell substrate by extracting regions corresponding to each viewing point from the captured test image and arranging the set of parallax image information displayed in the extracted regions of the captured test image for each parallax image of the test image displayed on the cell substrate before bonding the lenticular lens to the cell substrate, the parallax image prediction being predicted respectively for each of the parallax images; and a determination apparatus configured to analyze the parallax image prediction to determine a presence of a defect in the cell substrate.

4. A method for inspecting a cell substrate which is to be bonded to a lenticular lens for use in an integral-imaging three-dimensional image display apparatus and includes a display region having an array of a plurality of sub-regions, each sub-region displaying a set of parallax image information obtained by dividing each of a plurality of parallax images, the method comprising:

causing the cell substrate as an inspection object to display a test image;

capturing the test image displayed on the cell substrate before bonding the lenticular lens to the cell substrate, the captured test image including a plurality of the set of parallax image information of the parallax images which are arranged in turn;

generating a parallax image prediction of the parallax image which can be obtained when the lenticular lens is bonded to the cell substrate by extracting regions corresponding to each viewing point from the captured test image and arranging the set of parallax image information displayed in the extracted regions of the captured test image for each parallax image of the test image displayed on the cell substrate before bonding the lenticular lens to the cell substrate, the parallax image prediction being predicted respectively for each of the parallax images; and analyzing the parallax image prediction to determine a presence of a defect of the cell substrate.

5. The method of the claim 4, wherein the test image displayed on the cell substrate includes only one parallax image selected from the plurality of parallax images.

\* \* \* \* \*